United States Patent [19]

Suarez, Jr.

[11] Patent Number: 5,282,812
[45] Date of Patent: Feb. 1, 1994

[54] CLAMP FOR USE IN VASCULAR SURGERY

[76] Inventor: Luis Suarez, Jr., 349 Bellview Blvd., Steubenville, Ohio 43952

[21] Appl. No.: 727,892

[22] Filed: Jul. 10, 1991

[51] Int. Cl.⁵ .............................................. A61B 17/00
[52] U.S. Cl. .................................. 606/158; 606/142; 227/901; 227/902; 206/340
[58] Field of Search ............... 606/142, 157, 158, 205, 606/206, 207; 81/300, 418; 206/339, 340; 227/901, 902

[56] References Cited

U.S. PATENT DOCUMENTS

| | | |
|---|---|---|
| 650,822 | 6/1990 | Cain . |
| 2,104,029 | 1/1938 | Eshman ................ 128/326 |
| 2,575,800 | 11/1951 | Eicher ..................... 32/63 |
| 2,748,773 | 6/1956 | Vacheresse, Jr. ........... 128/326 |
| 2,887,110 | 5/1959 | Roeschmann ............. 128/321 |
| 3,032,039 | 5/1962 | Beaty ........................ 606/142 |
| 3,033,204 | 5/1962 | Wood ....................... 128/326 |
| 3,040,747 | 6/1962 | Wood ....................... 128/326 |
| 3,056,408 | 10/1962 | Brown ...................... 128/325 |
| 3,175,556 | 3/1965 | Wood ....................... 128/305 |
| 3,254,649 | 6/1966 | Wood ....................... 128/321 |
| 3,270,745 | 9/1966 | Wood ....................... 128/325 |
| 3,326,216 | 6/1967 | Wood ....................... 128/325 |
| 3,344,649 | 10/1967 | Wood ......................... 72/392 |
| 3,857,396 | 12/1931 | Hardwick .................. 128/335 |
| 4,073,179 | 2/1914 | Hickey et al. ................ 72/49 |
| 4,076,120 | 2/1978 | Carroll et al. ............. 206/340 |
| 4,146,130 | 3/1979 | Samuels et al. ............ 206/340 |
| 4,390,019 | 6/1983 | LeVeen et al. ............. 606/158 |
| 4,397,312 | 8/1983 | Molko ....................... 128/325 |
| 4,487,204 | 12/1984 | Hrouda ..................... 128/325 |
| 4,487,394 | 12/1984 | Rothfuss et al. ............ 254/28 |
| 4,511,035 | 4/1985 | Alpern ...................... 206/339 |
| 4,570,633 | 2/1986 | Golden ..................... 128/325 |
| 4,602,631 | 7/1986 | Funatsu .................... 128/321 |
| 4,616,651 | 10/1986 | Golden ..................... 128/325 |
| 4,635,634 | 1/1987 | Santos ...................... 606/142 |
| 4,671,282 | 6/1987 | Tretbar ..................... 128/346 |

Primary Examiner—Stephen C. Pellegrino
Assistant Examiner—Gary Jackson
Attorney, Agent, or Firm—Porter, Wright, Morris & Arthur

[57] ABSTRACT

A surgical clamp for the temporary occlusion of a blood vessel during a surgical procedure and forceps-like instruments co-operative with the clamp for application and removal of the clamp in a coherent and rational surgical system is described.

19 Claims, 2 Drawing Sheets

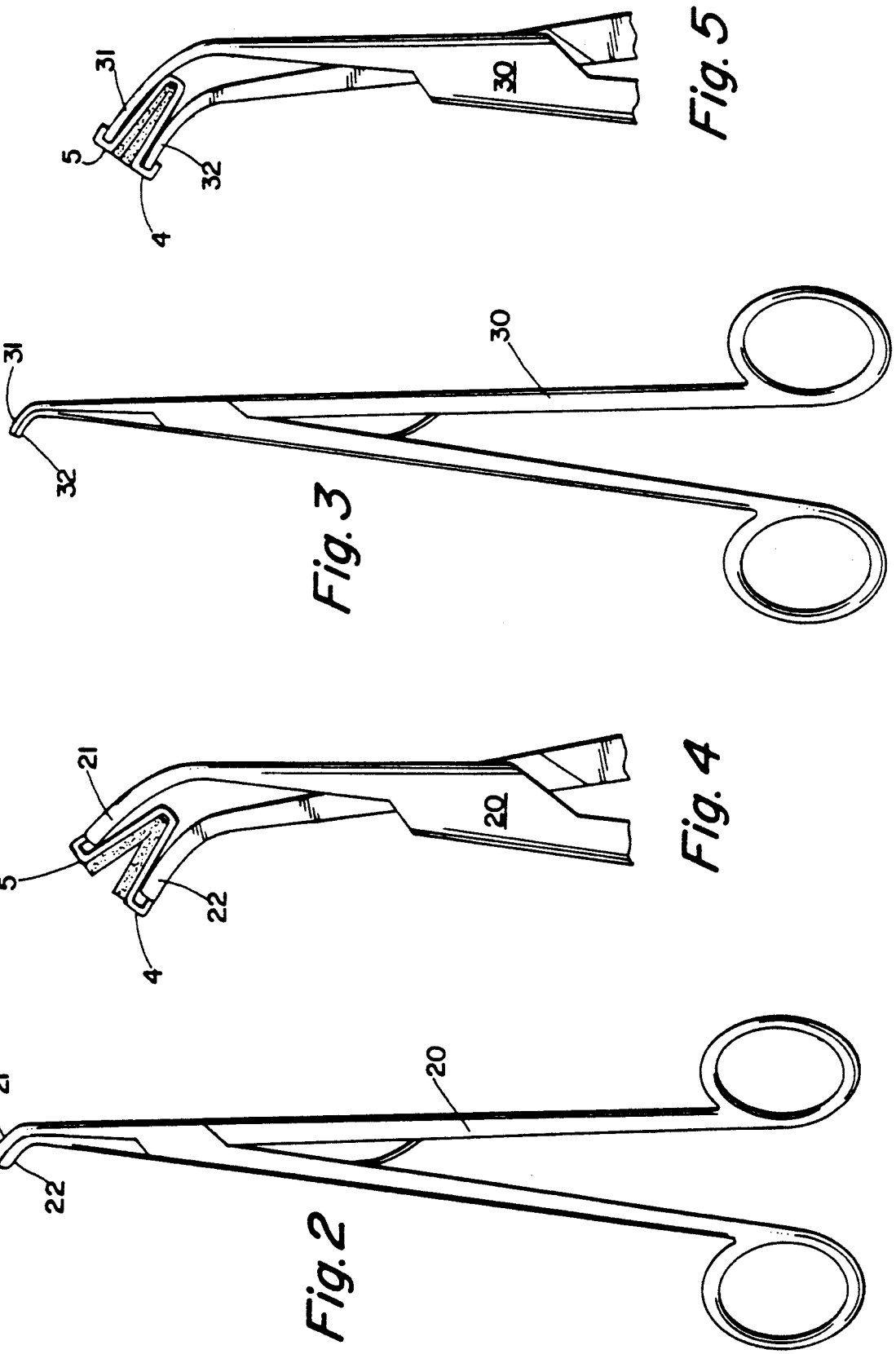

CLAMP FOR USE IN VASCULAR SURGERY

FIELD OF THE INVENTION

This invention relates to a clamping means useful in surgical operations for temporarily occluding blood vessels in the course of a surgical procedure.

BACKGROUND AND SUMMARY OF THE INVENTION

Many vascular surgical procedures require that the segment of a blood vessel on which a surgical procedure is to be performed be temporarily occluded. Such procedures include the removal of interior plaque from blood vessels deposited as a result of an arteriosclerotic condition, the repair of blood vessels damaged by rupture, accidents or gunshot wounds, bypass surgery, and the like.

In such procedures, an incision in the predetermined area of the vascular abnormality is made. In the prior art, clamps, known in the medical field as "Bulldog" clamps, are used to isolate a vascular segment of interest within the area of the incision.

Bulldog clamps are described in U.S. Pat. Nos. D268523, D276461, and D278654 and are used in conjunction with a clamp applier, which is either straight or curved and approximately 21.5 centimeters in length. Bulldog clamps include a variety of separately sized and configured disposable clamps capable of applying clamping pressures in various ranges extending from 10-15 grams up to 165-175 grams.

Other hemostasis clamps and clamp introducing and applying forceps are also known under trademarks such as "Hemoclips", "Ligoclips", and "Surgiclips".

One problem encountered in the prior art is that the clamps, the clamp appliers, or forceps used to apply the clamps may interfere with the access of other instruments to a limited surgical area, which is often times delimited by a four to five inch (4.0-5.0") incision.

It is an object of this invention to provide a removable (and disposable) clamp and a means for the insertion and removal of the clamp that is useful in vascular surgical procedures.

It is a further object to provide a clamping means capable of being provided in different sizes and which clamping means is readily inserted by one instrument and removed by another in the course of vascular surgery. In this manner, the clamping means of the invention will not otherwise interfere with the area of surgical interest. Because the inserter and removal instruments are different and co-act with the clamps in different ways, the clamps can be unmistakably inserted and removed. Thus, it is a further object of this invention to provide a coherent and rationally structured surgical clamping system for vascular procedures.

These and other objects of the invention can be further understood with reference to the following description of the preferred embodiment taken in conjunction with the drawings in which:

BRIEF DESCRIPTION OF THE DRAWINGS

FIG. 2 shows a clamp inserter.

FIG. 3 shows a clamp remover.

FIG. 4 shows a relationship of the clamp and the clamp inserter instrument.

FIG. 5 shows a relationship of the clamp and the clamp remover instrument.

DESCRIPTION OF THE PREFERRED EMBODIMENT

Figure 1:
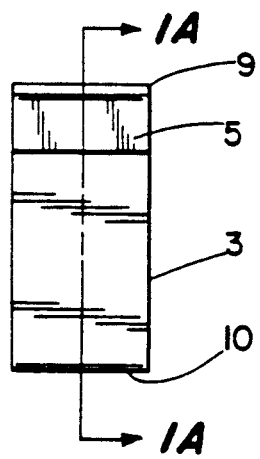
FIG. 1 shows a plan view.

As shown in FIG. 1, the clamp is formed from a material which is a surgically acceptable, bendable metal, such as a physiologically acceptable stainless steel alloy, or a polymeric or other material having a positional memory for an "open" and/or "closed" position. The material should have a shape retaining characteristic for each of the operative positions of the clamp while in use, i.e., once inserted and closed, the clamp should remain closed for the duration of the surgical procedure, until the procedure concludes and the clamp is opened and removed. A metal alloy of the gauge and type approximating that currently used in conventional surgical staples possesses such an ability.

Figure 1A:
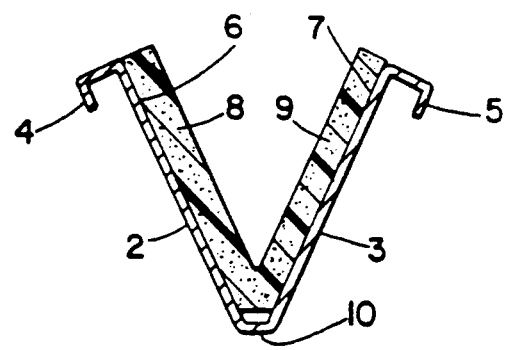
FIG. 1A shows a side view and FIG. 1B shows a perspective view of a removable clamp.
Figure 1B:
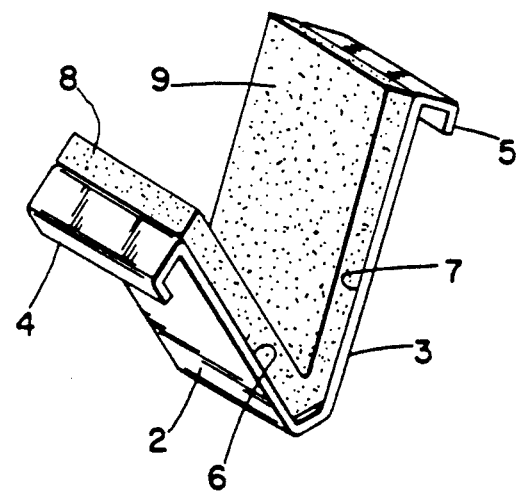

With reference to FIGS. 1, 1A and 1B, the clamp 1 is initially formed from a shape retaining material having the positional memory described above, in essentially a "V" shape having opposing side sections 2, 3 each of which includes extending "ears" 4, 5 at the uppermost part of the "V." The interior facing surfaces 6, 7 of the clamp are lined with a resilient material, 8, 9 such as a foam or polymer plastic resin composition which provides a cushion between the metal side sections 6, 7 of the clamp and the vascular segment to which the clamp is applied. The clamp is "bendable" along a transverse line at the "point" of the "V" at 10. The clamp thus comprises an integral member having a shape retaining characteristic and a bendable section with a positional memory. The pair of oppositely juxtaposed facing sections is capable in a first "open" position of surrounding a blood vessel section and capable in a second "closed" position of compressing the blood vessel section with pressure sufficient to occlude blood flow through the section of the blood vessel beyond the clamp. The interior facing clamp sections include on the interior sides a means for cushioning (i.e., reducing trauma injury as a result of compression) vascular tissue when the clamp is in the second closed position. The cushioning means may be integral or separately applied to the clamp. On the exterior sides of each facing section proximate to a terminal end thereof, the ear sections are provided which are operatively engageable as described below with the end tips of a surgical forceps-like inserter and remover.

The ear sections may be integrally formed from the bendable material and extend from a transverse line across each of the facing sections at approximately the terminal ends of the cushioned operative section of the clamp. To form the ear the material is shaped or folded over on itself to create essentially parallel channel sections between the folded over segment and the outer surface of the facing section.

In the application of the clamp, the inserter instrument, such as shown in FIG. 2, is employed. The instrument 20 is in the shape, size and operational configuration of a conventional forceps; however, in the utilization of the inserter instrument with the clamps of the invention, the tips 21, 22 of the inserter instrument are sufficiently broad to extend beyond the ears of the clamps so that forward pressure may be applied to push, when the clamp is open, the clamp over the vascular section of interest. After the section is fully surrounded by the clamp, the inserter instrument is squeezed and the clamp is closed, squeezing and temporarily occluding blood flow in the vessel to which the clamp is applied. As shown in FIG. 4, the frontal tips 21, 22 of the forceps-like mechanism are sufficiently broad to extend beyond the ear sections 4, 5 of the clamp. The inserter tips are capable of grasping the clamp in an open position and exerting sufficient force on the clamp to close the clamp and compress the blood vessel, for example, as shown in FIG. 6.

Figure 6:
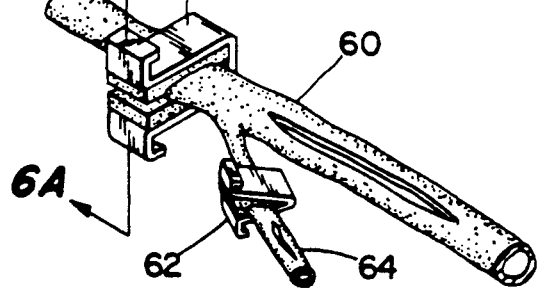
FIG. 6 shows a clamp applied to a vascular section.

In a typical surgical procedure, multiple clamps are applied (for example, as shown in FIG. 6) to temporarily occlude blood flow in the vascular section of interest, which usually is an artery or vein 60 and its proximate branches, e.g., 64.

After the relevant procedure is performed, the clamps are removed by the clamp removal instrument 30 shown in FIG. 3 which is similarly analogous to conventional forceps, but has tips 31, 32 which, unlike the larger tips of the inserter instrument, are reduced in size to fit within the clamp ears 4, 5. To remove the clamp, the tips of the removal instrument are first inserted over the clamp such that the tips 31, 32 are engaged within the ears 4, 5 on both sides of the clamp. In this first relationship, the tips of the removal instrument are then expanded, and the clamp is reopened to its original "V" shape and can be removed from the vascular vessel. A preferred angular orientation of the forceps tip from the central axis of the forceps handles is from about 30° to about 45° as shown in FIG. 2 and FIG. 3. The outer surfaces of the clamps and/or the jaw tips of the inserter and remover forceps may be provided with grip enhancing surfaces to ensure positive grasping of the clamp. The configuration of the jaw tips and the pivot point offset of the forceps instruments are suitably adopted to provide optimum engagement of the clamp (having its own predetermined configuration) by each of these single purpose instruments.

EXAMPLE

The clamp system of the invention is employed in a representative vascular surgery intended to remove plaque caused by arteriosclerosis.

An approximately four inch (4.0") incision is made in the groin and the clamp applier 20 is used to insert a clamp, or multiple clamps, as necessary, to temporarily occlude blood flow incoming to the artery. As needed, the clamps are applied to side branches of the artery such that the artery segment is fully occluded and blood flow in the artery is completely interrupted. The artery can then be opened, the plaque purged or removed, and the artery then sutured and closed. Upon completion of the procedure, the remover instrument 30 is employed to remove the previously applied clamps.

Use of the system of the invention results in a cleaner and less encumbered work area for the surgeon. The small size of the clamps results in a better defined work area and the interruption of the blood flow achieved reduces incidents of extraneous blood spurts and splashing.

A typical femoral artery is approximately one-fourth inch (0.25") in diameter and an appropriately sized clamp for application to such a blood vessel would be about one-half inch (0.5") in length with a width of about up to one-fourth inch (0.25") or more. Other sized clamps are likewise useful. For example, a size of approximately one-fourth inch by one-fourth inch (0.25"×0.25") is useful for medium to small blood vessels. The clamps can also be supplied in sets to provide predetermined discrete pressure ranges within the overall range of clamping pressures from about 10 to 175 grams. In ranges, individual clamps in separate sets would be capable of exerting pressures, for example, in the ranges of 10-15 grams, 20-25 grams, 25-30 grams, 50-60 grams, 75-80 grams, or 165-175 grams; or low and high pressure; or low, medium and high pressure; or other discrete predetermined ranges, depending on parameter choice and physiological necessity. Clamp size, in a range of clamps useful in applying different pressures for differing surgical procedures and environments, is a matter of design choice for a particular application. Several discrete sizes, applying different predetermined clamping pressures, can be standardized as are conventional clamps.

As a coherent surgical apparatus, clamps and appropriately sized inserter and remover forceps should be provided as a single set of components, all co-operatively useful with the other elements of the set components. Different sized sets of clamps and forceps instruments may be included in an integrated set of components. Or the same forceps may be adopted for use with clamps of differing sizes.

While foregoing reference is made to a "V" shaped clamp, it is evident that, as the clamp is lined with a rubber, polymeric, silastic elastomeric, sponge or foam cushion material, the lower point termination, including the bendable section, of an actual sharply pointed "V" shape may result in or interfere with a full closing of the clamp and result in the application of uneven force. Thus, the reference to a "V" shape herein, also includes reference to a foreshortened "V" (or more typically a "U" shape) in which, when the clamp is closed, the oppositely facing cushioned interior sections of the clamp are essentially maintained parallel to each other and apply approximately equal pressure along the length of the sides of the clamp to both sides of the vascular vessel effectively to interrupt blood flow. Such a "V" configuration may include more than one transverse bendable section, typically at the base of the "V" or at the figurative corners of a "U", operative when the clamp is closed and opened.

Figure 6A:
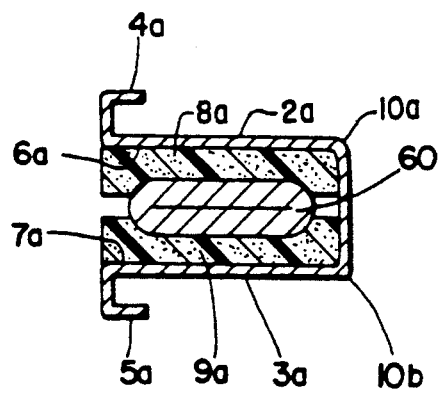
FIG. 6A is a cross-sectional view of one form of a clamp in operational relationship applied to a blood vessel.
Figure 6B:
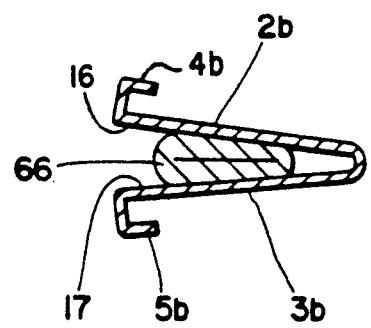
FIG. 6B is a cross-sectional view of another alternate form of the clamp applied to a blood vessel.

The practical application of the clamp is illustrated in FIG. 6, showing blood vessel 60 in which a surgical incision 65 is made. Clamp 61 is applied to the vessel and smaller clamp 62 is applied to a side branch vessel 64. (Clamping configuration is a matter of surgical choice dependent upon the vessel and procedure involved.) In the cross-section 6A—6A shown in FIG. 6A, a "U" shaped clamp, having bendable sections at 10a, 10b, is shown operatively disposed to occlude vessel 60. In the variation of FIG. 6A, ears 4a, 5a extend from section 2a, 3a, having the inner surfaces 6a, 7a that include the resilient liners 8a, 9a. In the cross-section shown in FIG. 6B, an alternative embodiment "V"-type clamp which includes as integral cushioning means, a smooth or polished interior surface 16, 17 integral with clamp walls 2b, 3b is shown. The clamp of FIG. 6B, also shown in the "closed" position occludes a vessel 66. The ears are at 4b, 5b.

Variations of the clamp, inserter and remover instrument and the coherent system described herein should be evident and can be made without departure from the spirit of the invention.

What is claimed is:

1. A surgical clamp for the temporary occlusion of a blood vessel in the course of a vascular surgical procedure comprising:

an integral member formed from a solid physiologically acceptable material including a bendable mid-section therein having a shape retaining characteristic, said member including on the sides of the bendable section, a pair of planar juxtaposed oppositely facing sections capable in a first open position of surrounding a portion of a blood vessel section and capable in a second closed position of compressing the blood vessel section with pressure sufficient to occlude blood flow through the section;

said integral member including on the interior sides of the planar facing sections a surface which is capable of cushioning vascular tissue when the member is in the second closed position; and said integral member having on the exterior sides of each facing section, an ear on each section formed from an "L"-shaped extension of the terminal end of the clamp which, in association with the outer surface of the clamp, forms a rectangular channel capable of receiving therein a correspondingly rectangular end tip of a surgical forceps.

2. A surgical clamp for the temporary occlusion of a blood vessel in the course of a vascular surgical procedure comprising:

an integral member formed from a physiologically acceptable material including a bendable section therein having a shape retaining characteristic, said member including on the sides of the bendable section, a pair of juxtaposed oppositely facing sections capable in a first open position of surrounding a portion of a blood vessel section and capable in a second closed position of compressing the blood vessel section with pressure sufficient to occlude blood flow through the section;

said integral member including an interior side on the facing section which is capable of cushioning vascular tissue when the member is in the second closed position; and said integral member having on the exterior sides of each facing section, an ear on each section which extends from a transverse line on the outer surface of the facing section which delineates the terminal end of the operative section of the clamp, said ear being an ear formed by material folded over at an end segment of the material forming the section which folded over material creates, an essentially parallel slot section between the folded over ear and the exterior outer surface of the material forming the facing section.

3. The clamp of claim 1 in which the facing sections include an integral member in the form of a "V" shape.

4. The clamp of claim 3 which the bendable section is defined at the approximate tip of the "V" shape.

5. The clamp of claim 1 in which the facing sections comprise parallel planar sides of an integral member in the form of a "U" shape.

6. The clamp of claim 1 including two bendable sections, said facing sections extending in parallel relationship from said bendable sections.

7. The clamp of claim 1 in which the outer surface of the clamp includes a grip enhancing surface.

8. The clamp of claim 1 in which the interior side of the facing section which is capable of cushioning includes a resilient material.

9. The clamp of claim 8 in which the resilient material is selected from the group of rubber, polymeric, silastic, elastomeric, sponge or foam materials.

10. The clamp of claim 1 in which in the closed position the integral member is capable of applying clamping pressures between the facing sections in predetermined ranges within the overall pressure range of from about 10 grams up to about 175 grams.

11. The clamp of claim 1 having a length not more than approximately 0.5 inch.

12. The clamp of claim 1 having a width not more than approximately 0.5 inch.

13. A surgical apparatus kit for temporarily occluding the flow of blood in a vessel during a vascular surgical procedure including:

(A) a clamp formed from a solid bendable material having a shape retaining characteristic including a pair of juxtaposed oppositely facing flat sections extending from a mid-section of the same integral element, capable in a first open position of surrounding a portion of a blood vessel section and capable in a second closed position of compressing the blood vessel with pressure sufficient to occlude blood flow;

said clamp including on the interior sides of each facing flat section a surface including means for cushioning vascular tissue when the member is in the second closed position;

said clamp having on the exterior sides of each facing section proximate to a terminal end thereof an ear section formed from an "L"-shaped extension of the terminal end of the clamp which, in association with the outer surface of the clamp, forms a rectangular channel capable of receiving therein the correspondingly rectangular end tip of a remover instrument;

(B) an inserter instrument including a forceps-like mechanism having a frontal tip section overlapping said rectangular channel and the terminal end of said L-shaped extension when one inner surface of said frontal tip section is in contact with an exterior side of a facing flat section of said clamp, which instrument includes jaws capable of grasping and holding the clamp at the exterior sides of the facing flat sections in an open position when the clamp surrounds a portion of a blood vessel section and of exerting sufficient force on the held clamp to close the clamp and compress the blood vessel; and (C) a remover instrument including a forceps-like mechanism having a frontal tip section capable of being inserted into the ear section of the clamp when the clamp is in a closed position and is further capable of opening and removing the clamp.

in which, the frontal tip section of at least one of the inserter and the remover instruments is oriented at an angle of approximately 30° to 45° from the central axis of the instrument.

14. The surgical apparatus of claim 13 in which the inner jaws of one of the inserter instruments and the remover instruments includes a grip enhancing surface.

15. The surgical apparatus of claim 13 including a plurality of clamps, said clamps capable of applying pressures between the facing sections in predetermined pressure ranges within the overall pressure range of from about 10 grams up to about 175 grams.

16. The surgical apparatus of claim 13 including a plurality of sets of clamps, each clamp in a set capable of applying pressure between the facing sections in a predetermined, discrete, pressure range determined for each of the sets of clamps.

17. A surgical apparatus kit for temporarily occluding the flow of blood in a vessel during a vascular surgical procedure including:

(A) two sets of clamps, each of said clamps formed from a solid bendable material having a shape retaining characteristic including a pair of juxtaposed oppositely facing sections extending from a midsection of the same integral element, capable in a first open position of surrounding a portion of a blood vessel section and capable in a second closed position of compressing the blood vessel with pressure sufficient to occlude blood flow;

each of said clamps including on the interior sides of each facing section a surface including means for cushioning vascular tissue when the member is in the second closed position;

each of said clamps having on the exterior sides of each facing section proximate to a terminal end thereof an ear section formed from an "L"-shaped extension of the terminal end of the clamp which, in association with the outer surface of the clamp, forms a slot capable of receiving therein a correspondingly shaped end tip of a remover instrument;

each clamp in a set capable of applying pressure between the facing section in a predetermined, discrete, pressure range determined for each of the sets of clamps;

one set of clamps capable of applying pressure sufficient to occlude a principal blood vessel, the other set of clamp capable of applying pressure sufficient to occlude adjacent branches of the principal vessel;

(B) an inserter instrument including a forceps-like mechanism having a frontal tip section overlapping said slot and the terminal end of said L-shaped extension when one inner surface of said frontal tip section is in contact with an exterior side of a facing section of said clamp, which instrument includes jaws capable of grasping and holding a clamp at the exterior sides of the facing sections of the clamp in an open position when the clamp surrounds a portion of a blood vessel section and of exerting sufficient force on the held clamp to close the clamp and compress the blood vessel; and (C) a remover instrument including a forceps-like mechanism having frontal tip sections insertable within the ear sections of a clamp and which, upon being inserted into the ear sections, the opening of the forceps tip opens the clamp, whereby the clamp may be removed, in which, the frontal tip section of at least one of the inserter and the remover instruments is oriented at an angle of approximately 30° to 45° from the central axis of the instrument.

18. The surgical apparatus of claim 16 including two sets of inserter and remover instruments adapted to each of the two sets of clamps.

19. The surgical apparatus of claim 16 in which the different clamps in the sets have equivalently sized ears, all of said clamps insertable by the same inserter and all of said clamps removable by the same remover.

* * * * *